US00PP11993P2

(12) United States Plant Patent
VandenBerg

(10) Patent No.: US PP11,993 P2
(45) Date of Patent: Jul. 17, 2001

(54) CHRYSANTHEMUM PLANT NAMED 'YODULUTH'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/383,534

(22) Filed: Aug. 26, 1999

(51) Int. Cl.[7] ..... A01H 5/00
(52) U.S. Cl. ..... Plt./286
(58) Field of Search ..... Plt./286, 297

*Primary Examiner*—Howard J. Locker
(74) *Attorney, Agent, or Firm*—C. A. Whealy

(57) ABSTRACT

A distinct cultivar of Chrysanthemum plant named 'Yoduluth', characterized by its upright, somewhat outwardly spreading and uniformly mounded plant habit; large vigorous plants; freely branching habit, full and dense plants; strong, dark green foliage; uniform flowering; nine-week response time; numerous large daisy-type inflorescences that are about 8.8 cm in diameter; dark purple and light pink-colored spoon-shaped ray florets with bright yellow-colored disc florets; and good postproduction longevity with inflorescences and leaves maintaining good substance and color for about three or four weeks in an interior environment.

2 Drawing Sheets

BACKGROUND OF THE INVENTION

The present invention relates to a new and distinct cultivar of Chrysanthemum plant, botanically know as *Dendranthema grandifora* and hereinafter referred to by the cultivar name Yoduluth.

The new Chrysanthemum is a product of a planned breeding program conducted by the Inventor in Salinas, Calif. The objective of the breeding program is to create new pot-type Chrysanthemum cultivars having desirable inflorescence forms and floret colors and good post-production longevity.

The new Chrysanthemum originated from a cross made by the Inventor in October, 1994, in Salinas, Calif., of the *Dendranthema grandifora* cultivar Rage, disclosed in U.S. Plant Pat. No. 8,770, as the female, or seed, parent, with the *Dendranthema grandiflora* cultivar Tijuana, disclosed in U.S. Plant Pat. No. 9,083, as the male, or pollen, parent.

The new Chrysanthemum was discovered and selected by the Inventor as a flowering plant within the progeny of the stated cross in a controlled environment in Alva, Fla., in April, 1996. The selection of this plant was based on its desirable inflorescence form and floret colors and good post-production longevity.

Asexual reproduction of the new Chrysanthemum by terminal cuttings harvested in a controlled environment in Alva, Fla., has shown that the unique features of this new Chrysanthemum are stable and reproduced true to type in successive generations.

SUMMARY OF THE INVENTION

The cultivar Yoduluth has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoduluth'. These characteristics in combination distinguish 'Yoduluth' as a new and distinct Chrysanthemum:

1. Upright, somewhat outwardly spreading and uniformly mounded plant habit.
2. Large vigorous plants.
3. Freely branching habit, full and dense plants.
4. Strong, dark green foliage.
5. Uniform flowering.
6. Nine-week response time.
7. Floriferous, numerous large daisy-type inflorescences that are about 8.8 cm in diameter.
8. Dark purple and light pink-colored spoon-shaped ray florets with bright yellow-colored disc florets.
9. Excellent postproduction longevity with inflorescences and leaves maintaining good substance and color for at least three weeks in an interior environment.

The new Chrysanthemum can be compared to the Chrysanthemum cultivar Rapture, disclosed in U.S. Plant Pat. No. 8,179. However in side-by-side comparsions in Salinas, Calif., and Leamington, Ontario, Canada, under commerical practice, plants of the new Chrysanthemum differ from plants of the cultivar Rapture in the following characteristics:

1. Plants of the new Chrysanthemum are more vigorous, taller and stronger than plants of the cultivar Rapture.
2. Plants of the new Chrysanthemum are more upright and less spreading than plants of the cultivar Rapture.
3. Plants of the new Chrysanthemum flower about four or five days later than plants of the cultivar Rapture.
4. Ray florets of the new Chrysanthemum are darker purple in color than ray florets of the cultivar Rapture.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph on the first sheet comprises a top perspective view of a typical flowering plant of 'Yodulth'.

The photograph on the second sheet comprises a close-up view of a typical inflorescence and upper (left) and lower (right) surfaces of typical leaves of the cultivar Yoduluth. Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commerical potted Chrysanthemum production. Four unrooted cuttings were directly stuck in a 15-cm container and pinched once. Plants used for this description were grown as spray-types. Measurements and numerical values represent averages of typical flowering plants.

Botanical classification: *Dendranthema grandiflora* cultivar Yoduluth.

Commercial classification: Daisy spoon spray-type pot Chrysanthemum.

Parentage:

*Female or seed parent.*—*Dendranthema grandiflora* cultivar Rage, disclosed in U.S. Plant Pat. No. 8,770.

*Male or pollen parent.*—*Dendranthema grandifora* cultivar Tijuana, diclosed in U.S. Plant Pat. No. 9,083.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy pot Chrysanthemum typically grown as a spray-type. Inverted triangle; large and vigorous with stems upright and somewhat outwardly spreading giving a uniformly mounded appearance to the plant. Freely branching; about four or five lateral branches develop after removal of terminal apex (pinching); dense and full plants.

*Plant height.*—About 33 cm.

*Plant width.*—About 37 cm.

*Stem color.*—144A.

*Stem texture.*—Pubescent.

*Foliage description.*— Arrangement: Alternate. Length: About 7.6 cm. Width: About 5.1 cm. Apex: Mucronate. Base: Attenuate. Margin: Palmately lobed, sinuses between lateral lobes mostly parallel. Texture: Upper and lower surfaces with very fine pubescence; veins prominent on lower surface. Petiole length: About 2.1 cm. Petiole width: About 3 mm. Color: Young foliage upper surface: 147A. Young foliage lower surface: Close to 147B. Mature foliage upper surface: 147A. Mature foliage lower surface: 147B. Venation upper surface: 147A. Venation lower surface: 147B.

Inflorescence description:

*Appearance.*—Daisy inflorescence form with spoon-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence inititation and development can be induced under short day/long night conditions (at least 13.5 hours of darkness). Plants exposed to three weeks of long day/short night conditions after planting followed by photoinductive short day/long night conditions flower about nine weeks later.

*Postproduction longevity.*—Inflorescences and leaves will maintain good color and substance for at least three weeks in an interior environment.

*Quantity of Inflorescences.*—Freely flowering; about six inflorescences per lateral branch or about 24 to 30 inflorescences per plant.

*Inflorescence bud.*— Height: About 6.5 mm. Diameter: About 7.5 mm. Color: Greener than 143 A.

*Inflorescence size.*— Diameter: About 8.8 cm. Depth (height): About 1.25 cm. Diameter of disc: About 1.8 cm.

*Ray florets.*— Shape: Spoon. Orientation: Initially upright, then perpendicular to peduncle. Aspect: Straight. Length: About 3.9 cm. Width: About 9 mm. Corolla tube length: About 1.7 cm. Corolla tube width: About 3 mm. Apex: Rounded to emarginate. Margin: Entire. Texture: Smooth, velvety. Number of ray florets per inflorescence: About 29; one whorl. Color: When opening, tube: Close to 72B. When opening, throat: 59A. Fully opened, tube, upper surface: 62B–62C to 70D. Fully opened, tube, lower surface: 70C–70D underlain with darker, 70A–70B, longitudinal streaks. Fully opened, throat: Close to 59B to 61A or slightly more red than 61A.

*Disc florets.*— Shape: Tubular. Apex: Serrated. Length: About 6.5 mm. Width: Apex, about 2 mm; base, about 1 mm. Number of disc florets per inflorescence: Numerous, about 112. Color: Immature: 144A. Mature: Apex: 9A. Mid-section: Light green. Base: White, 155D.

*Reproductive organs.*— Androecium: Present on disc florets only. Anther color: 9A. Pollen amount: Scarce to moderate. Pollen color: 14A. Gynoecium: Present on both ray and disc florets.

Disease resistance: Resistance to pathogens to common to Chrysanthemums has not been observed on plants grown under commercial greenhouse conditions.

Seed production: Seed production has not been observed.

It is claimed:

1. A new and distinct cultivar of Chrysanthemum plant named 'Yoduluth', as illustrated and described.

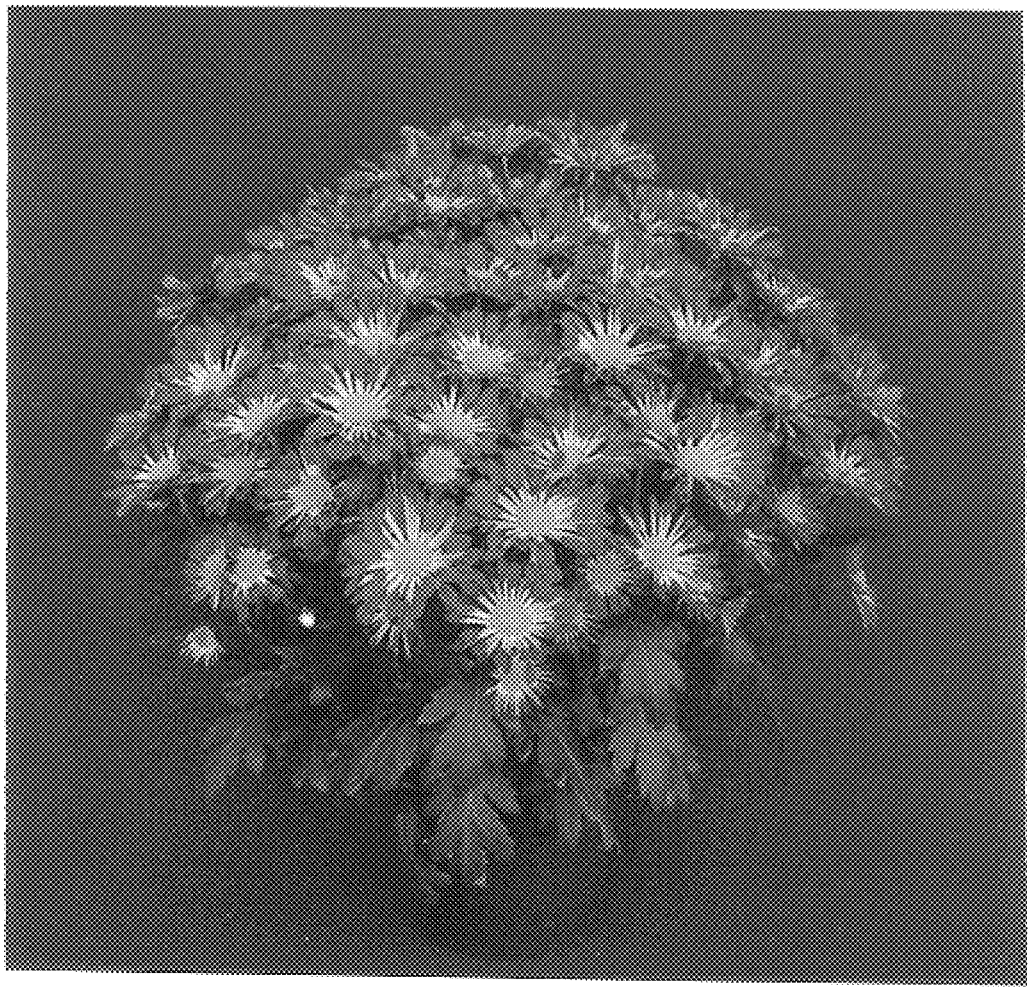

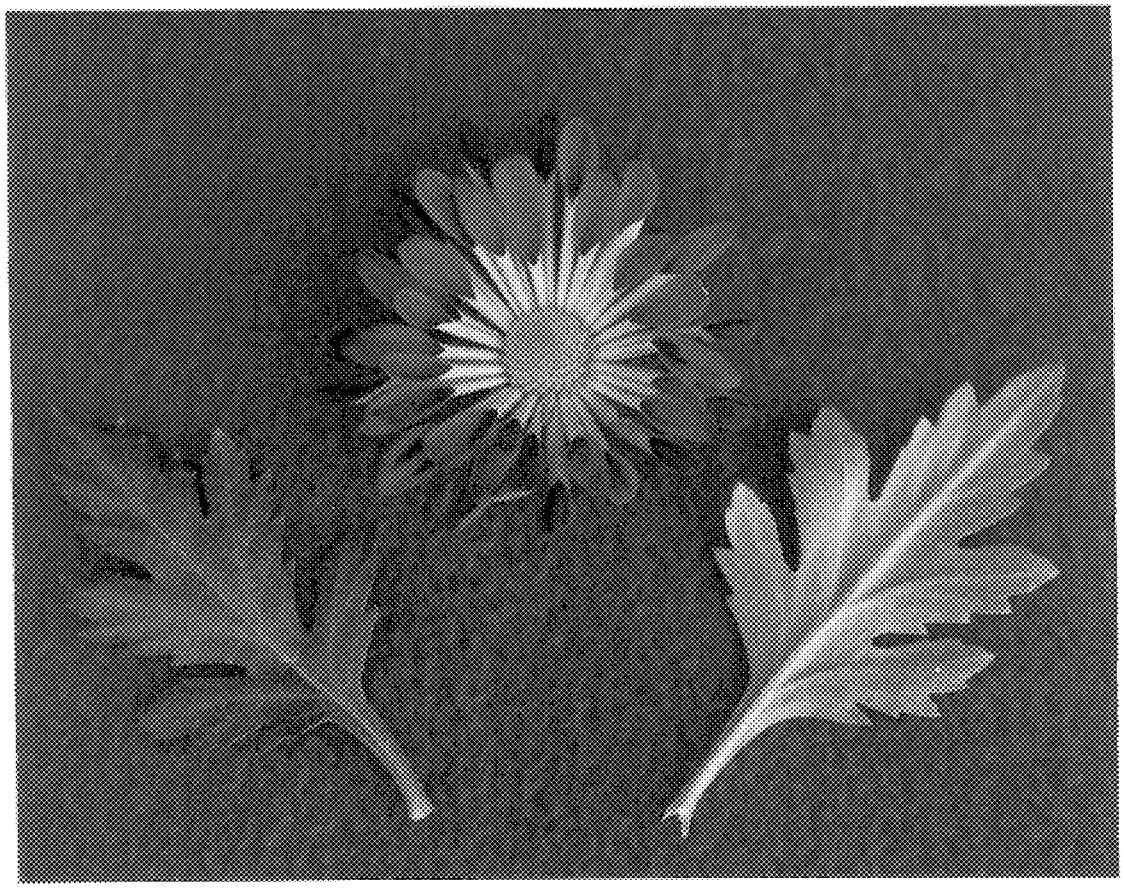

* * * * *